(12) United States Patent
Otsubo et al.

(10) Patent No.: US 7,458,960 B2
(45) Date of Patent: *Dec. 2, 2008

(54) PULL-ON DISPOSABLE DIAPER

(75) Inventors: Toshifumi Otsubo, Kagawa-ken (JP);
Shunsuke Takino, Kagawa-ken (JP)

(73) Assignee: Uni-Charm Co., Ltd, Ehime-Ken (JP)

( * ) Notice: Subject to any disclaimer, the term of this patent is extended or adjusted under 35 U.S.C. 154(b) by 34 days.

This patent is subject to a terminal disclaimer.

(21) Appl. No.: 11/056,283

(22) Filed: Feb. 14, 2005

(65) Prior Publication Data

US 2005/0148989 A1 Jul. 7, 2005

Related U.S. Application Data

(63) Continuation of application No. PCT/JP2003/010312, filed on Aug. 13, 2003.

(30) Foreign Application Priority Data

Aug. 30, 2002 (JP) .............................. 2002-252969
Jul. 14, 2003 (JP) .............................. 2003-196206

(51) Int. Cl.
*A61F 13/15* (2006.01)
*A61F 13/20* (2006.01)

(52) U.S. Cl. ................................. 604/385.201; 604/367

(58) Field of Classification Search ............ 604/385.01, 604/385.201

See application file for complete search history.

(56) References Cited

U.S. PATENT DOCUMENTS

| | | | | |
|---|---|---|---|---|
| 3,731,688 A | * | 5/1973 | Litt et al. ..................... | 604/365 |
| 3,968,799 A | * | 7/1976 | Schrading .................... | 604/365 |
| 4,670,011 A | * | 6/1987 | Mesek ......................... | 604/378 |
| 6,723,892 B1 | * | 4/2004 | Daley et al. .................. | 604/378 |

| | | |
|---|---|---|
| 2004/0133178 A1 | 7/2004 | Otsubo et al. |
| 2005/0038404 A1 | 2/2005 | Takino et al. |

FOREIGN PATENT DOCUMENTS

| | | | |
|---|---|---|---|
| EP | 1 177 782 A1 | | 2/2002 |
| EP | 1177782 A1 | * | 2/2002 |
| EP | 1 219 273 A2 | | 7/2002 |
| JP | 47-36734 | | 12/1972 |
| JP | 48-20638 U | | 3/1973 |

(Continued)

*Primary Examiner*—Tatyana Zalukaeva
*Assistant Examiner*—Melanie J Hand
(74) *Attorney, Agent, or Firm*—Lowe Hauptman Ham & Berner, LLP

(57) ABSTRACT

A pull-on disposable diaper is composed of front and rear waist covering regions and a crotch covering region and has a body fluid absorbing component extending over the crotch covering region and further extending into the front and rear waist covering regions. In the crotch covering region, the body fluid absorbing component is folded toward a center line A-A and covered with a liquid-pervious cover sheet. The cover sheet extends in the transverse direction of the absorbing component over an inner surface of the absorbing component and further extends to the side of an outer surface of the absorbing component. On the outer surface of the absorbing component, transversely opposite lateral edges of the cover sheet are folded back outward in the transverse direction. The folded-back lateral edges are joined to the inner surface of the sheet defining the crotch covering region.

5 Claims, 6 Drawing Sheets

FOREIGN PATENT DOCUMENTS

| | | |
|---|---|---|
| JP | 50-21845 | 3/1975 |
| JP | 50-33044 | 3/1975 |
| JP | 50-33044 A | 3/1975 |
| JP | 56-34345 | 4/1981 |
| JP | 60-163911 | 10/1985 |
| JP | 63-32516 U | 3/1988 |
| JP | 11-188062 | 7/1999 |
| JP | 2002-035033 | 2/2002 |
| JP | 2003-010244 | 1/2003 |
| JP | 2003-220091 | 8/2003 |
| JP | 2003-230594 | 8/2003 |

* cited by examiner of direction. Simultaneously, the diaper 201 is tucked from its
PULL-ON DISPOSABLE DIAPER

BACKGROUND OF THE INVENTION

This invention relates to a pull-on disposable diaper.

Japanese Patent Application No. 1975-33044A discloses a foldup-type disposable diaper 201 as shown in FIG. 10 of the accompanying drawings. This diaper 201 is composed of a liquid-absorbent pad, a liquid-pervious inner sheet 222 and a liquid-impervious outer sheet 223 so as to have a rectangle shape and then folded along a transversal 210a orthogonal to long sides of the diaper 201 in two halves in a longitudinal direction. Simultaneously, the diaper 201 is tucked from its transversely opposite edges inwardly of the diaper, more specifically, toward a middle point of the transversal 210a so as to form pockets 218. This diaper 201 is adapted to be worn in combination with use of a diaper cover and surface sections of the sheet 223 facing each other as the diaper 201 is tucked inward in this manner are partially joined in order to prevent the respective pockets 218 might get out of initial shapes thereof even after the diaper 201 has been developed to be put on a wearer's body. The diaper arranged in such manner is effective to avoid leakage of body fluids regardless of its rectangular shape because a region of the diaper destined to cover the wearer's crotch is sufficiently narrow to be placed closely against the wearer's crotch.

Japanese Utility Model Application No. 1972-36734A discloses a foldup-type diaper made from a rectangular strip. This diaper also is adapted to be worn in combination with use of a diaper cover and the diaper is tucked inward from its transversely opposite edges in a longitudinally middle zone of the diaper. The crotch region of the diaper obtained in this manner has its width sufficiently reduced to be placed closely against the wearer's crotch and thereby to alleviate an anxiety of sideways urine leakage.

The diaper disclosed in Japanese Patent Application No. 1975-33044A intends to prevent the diaper from getting out of its initial shape by partially joining together the surface sections opposed to each other as the diaper is folded and tucked. However, such joining may obstruct the diaper to be flatly developed and retard operation of putting the diaper on the wearer's body.

The diaper disclosed in the above-cited Japanese Utility Model Application No. 1972-36734A is accompanied with an inconvenience that the crotch region folded and tucked in this manner may get out of its desired shape as the diaper is put on the wearer's body.

SUMMARY OF THE INVENTION

It is an object of this invention to provide a pull-on disposable diaper having a body fluid absorbing component partially folded inward in a crotch covering region improved so that zones of the body fluid absorbing component folded inward can be reliably maintained in such a folded state even if these folded zones are not joined such as in the prior art.

In accordance with this invention, there is a pull-on disposable diaper having a height direction, a width direction being orthogonal to the height direction and a back-and-forth direction, the diaper being substantially symmetric about a center line bisecting a dimension of the diaper in the width direction, the diaper comprising a covering component made of sheet material having an inner surface facing a wearer's body and outer surface facing a wearer's clothes and composed of front waist covering region destined to cover a wearer's front waist, a rear waist covering region destined to cover a wearer's rear waist and a crotch covering region destined to cover a wearer's crotch so as to define a pants-like configuration having a waist-hole and a pair of leg-holes, and a body fluid absorbing component extending over the crotch covering region and further extending into the front and rear waist covering regions.

The pull-on disposable diaper further comprises the body fluid absorbing component comprising a liquid-absorbent core and a liquid-pervious cover sheet. The core have an inner surface facing the wearer's body, an outer surface facing away from the wearer's body and side surfaces extending between the inner and outer surfaces in the height direction and extending beyond the crotch covering region into the front and rear waist covering regions. The cover sheet covers the inner surface, the side surfaces and at least a part of the outer surface of the core. The body fluid absorbing component is formed in the crotch covering region with a first folding guide extending from a middle zone between transversely opposite lateral edges extending parallel to each other in the height direction to the respective lateral edges in the front waist covering region so as to describe a generally V-shape, a second folding guide extending to the respective lateral edges in the rear waist covering region so as to describe a generally V-shape and a third folding guide, extending in the width direction between the first and second folding guides. The absorbing component is folded on both sides of the center line along the third folding guide so that the core has its outer surface sections facing to each other and along the first and second folding guides so that the core has its inner surface sections facing to each other, transversely opposite lateral edges of the cover sheet is folded back outward in the width direction on the outer surface of the core and is joined to the inner surface of the sheet material defining the crotch covering region.

This invention includes the following embodiments.

The outer surface of the core is covered at least with the cover sheet and a liquid-impervious sheet lying outside the cover sheet and defining the crotch covering region.

The outer surface of the core is covered with the cover sheet, a nonwoven fabric lying outside the cover sheet, a plastic film lying outside the nonwoven fabric and defining the liquid-impervious sheet and a nonwoven fabric lying outside the liquid-impervious sheet.

DETAILED DESCRIPTION OF THE PREFERRED EMBODIMENTS

Details of the pull-on disposable diaper according to this invention will be more fully understood from the description given hereunder with reference to the accompanying drawings.

Figure 1:
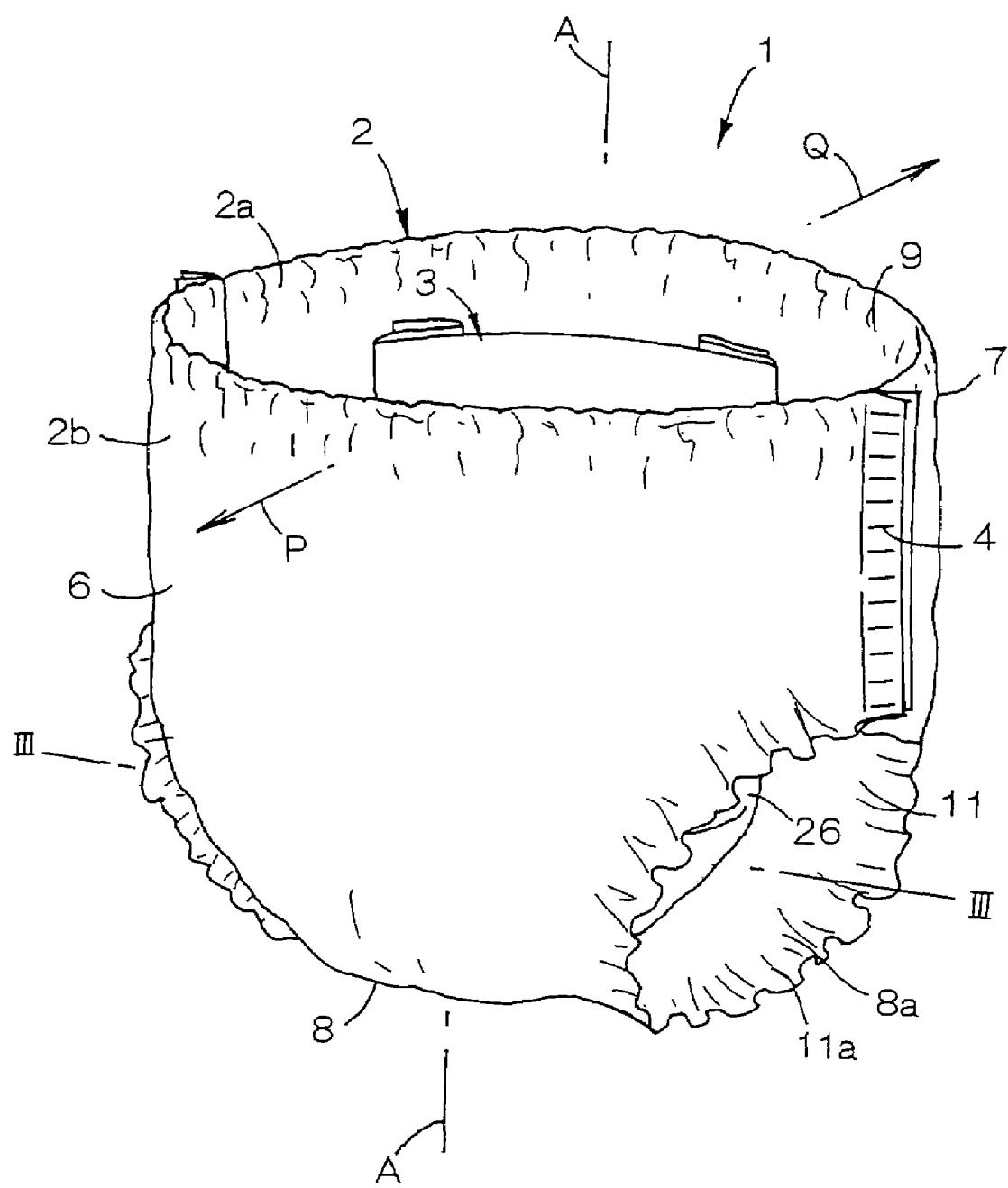
FIG. 1 is a perspective view showing a pants-type disposable diaper.
Figure 2:
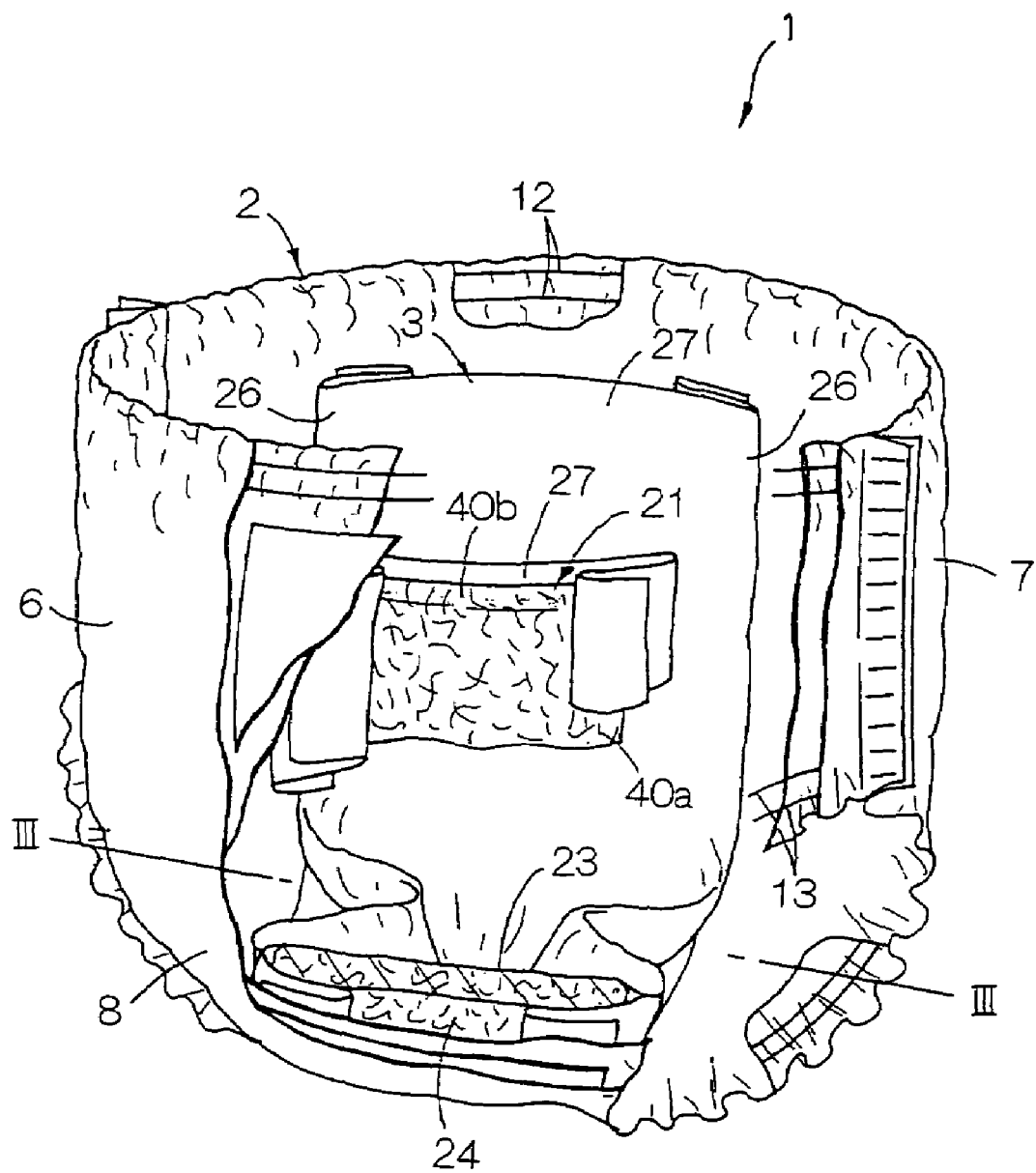
FIG. 2 is a partially cutaway perspective view showing the diaper of FIG. 1.
Figure 3:
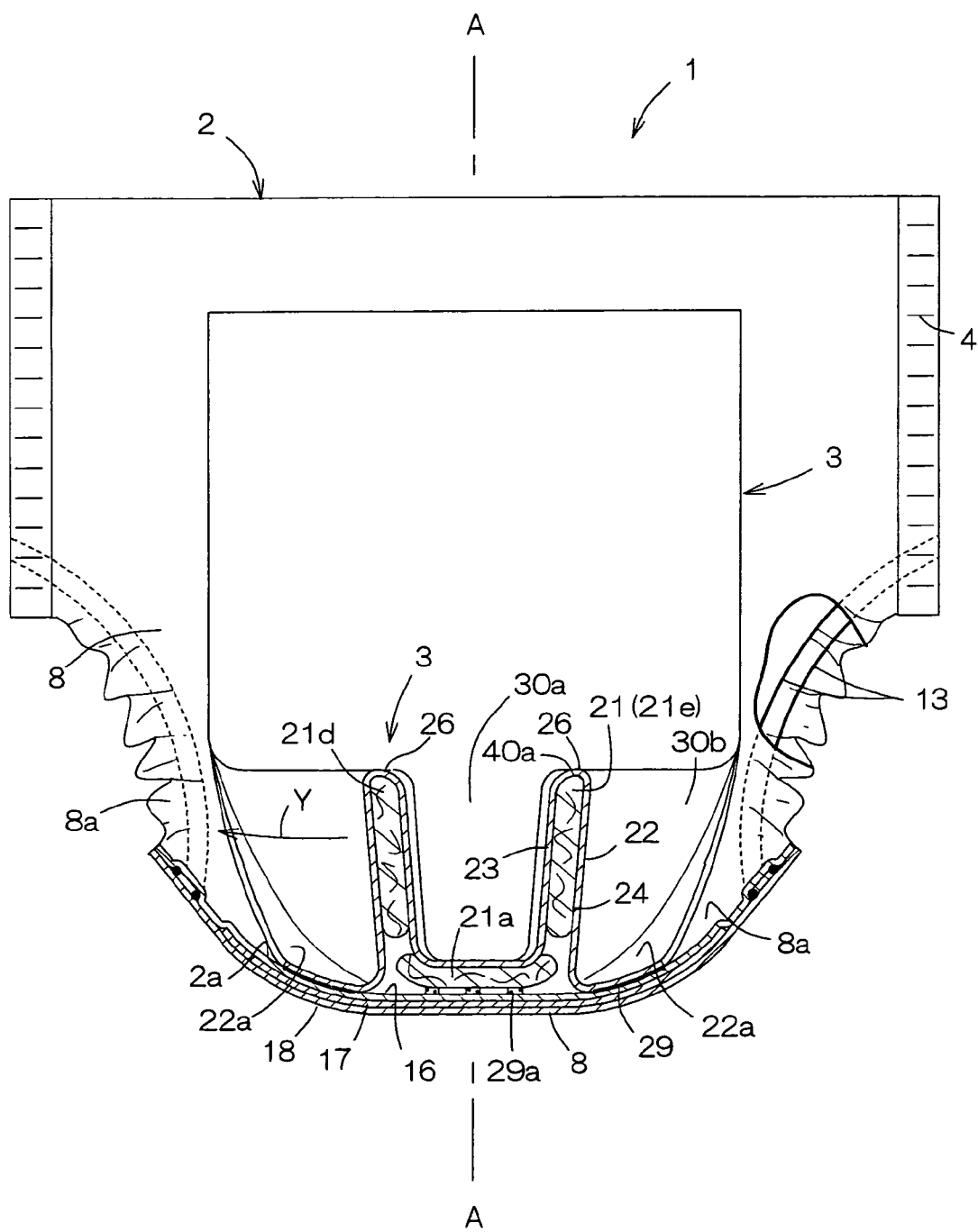
FIG. 3 is a sectional view taken along a line III-III in FIG. 1.

FIG. 1 is a perspective view showing a pull-on disposable diaper 1, FIG. 2 is a partially cutaway perspective view showing this diaper 1 and FIG. 3 is a sectional view taken along a line III-III in FIG. 1. The diaper 1 has height and width directions orthogonal to each other and a back-and-forth direction. The height direction corresponds to a vertical direction in FIG. 1, the back-and-forth direction corresponds to a direction indicated by a double-headed arrow P-Q in FIG. 1 and the width direction corresponds to a right-and-left direction as viewed in FIG. 3. The diaper 1 basically comprises a pants-like covering component 2 and a body fluid absorbing component 3 for containment of body fluids absorbed therein. The covering component 2 is formed by sheet material such as a nonwoven fabric or plastic film and has an inner surface 2a facing a diaper wearer's body and an outer surface 2b facing the wearer's clothes. This covering component 2 is composed of a front waist covering region 6, a rear waist covering region 7 and a crotch covering region 8 adapted to cover wearer's front, rear and crotch regions, respectively. The front and rear waist covering regions 6, 7 are overlaid together along transversely opposite lateral marginal edges of the diaper 1 and joined together along these opposite lateral marginal edges at a plurality of joining zones 4 arranged intermittently in a vertical direction along these opposite lateral marginal edges so that the front waist covering region 6, the rear waist covering region 7 and the crotch covering region 8 cooperate with one another to define a waist-hole 9 and a pair of leg-holes 11. The waist-hole 9 and the leg-holes 11 are provided along peripheral marginal edges thereof with a waist-circumferential elastic member 12 and leg-circumferential elastic members 13 attached in a stretched state thereto, respectively. The body fluid absorbing component 3 lies on the inner surface 2a of the covering component 2 so as to extend over the crotch covering region 8 and to extend further into the front and rear waist covering regions 6, 7. The body fluid absorbing component 3 is folded toward a longitudinal center line A-A (See FIG. 4 also) bisecting a width of the diaper 1, i.e., folded inward in a transverse direction of the diaper 1 so that the body fluid absorbing component 3 may have its width reduced in the crotch covering region 8.

Figure 4:
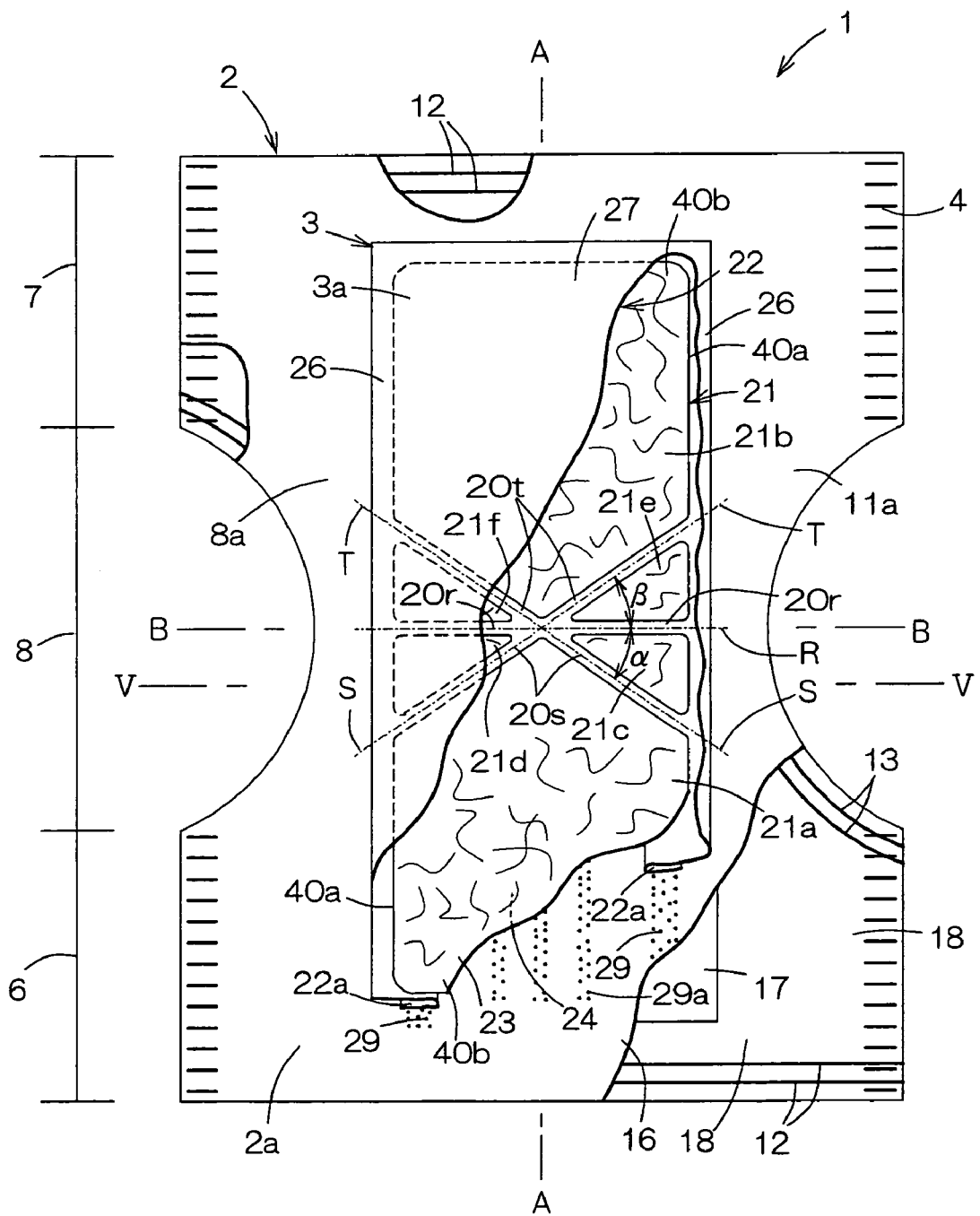
FIG. 4 is a developed view of the diaper of FIG. 1.
Figure 5:
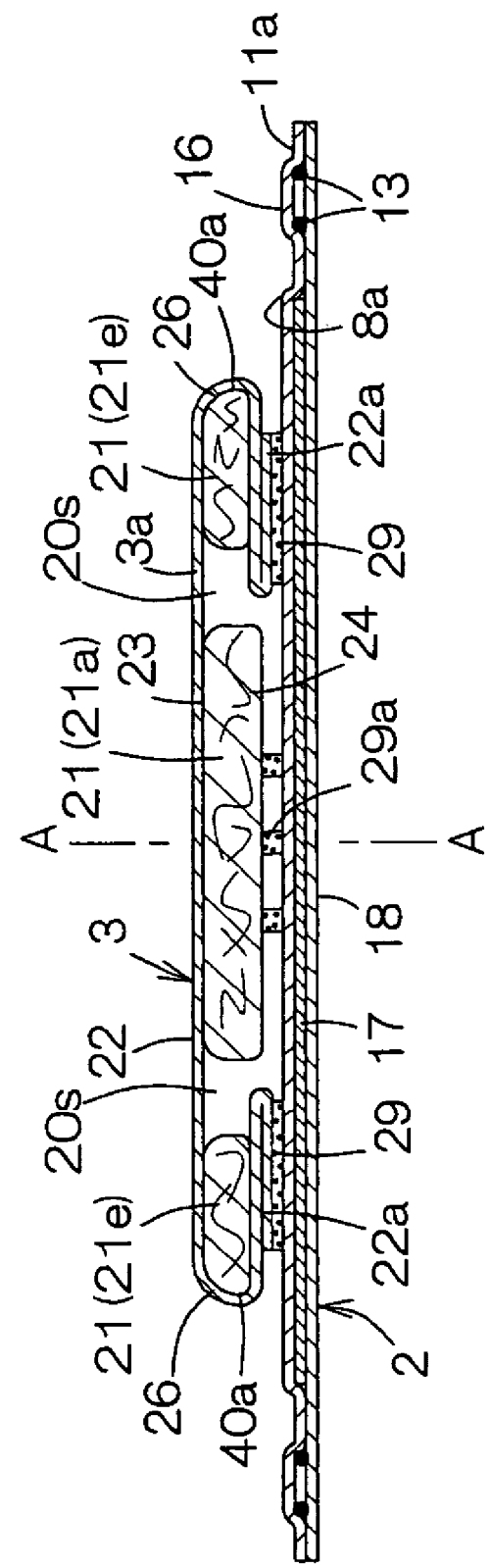
FIG. 5 is a sectional view taken along a line V-V in FIG. 4.
Figure 6:
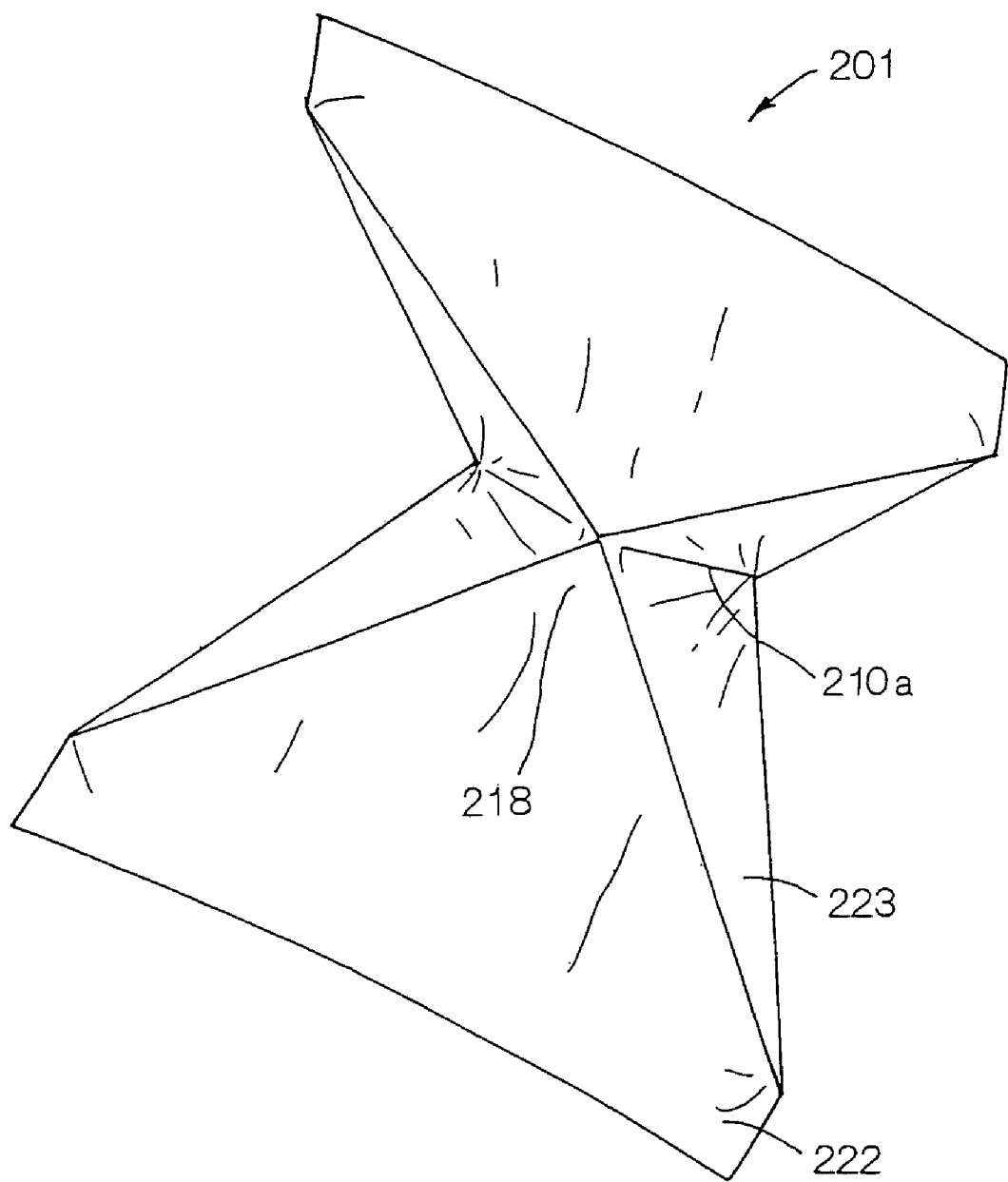
FIG. 6 is a perspective view showing an example of the conventional diaper.

FIG. 4 is a partially cutaway plan view showing the diaper 1 of FIG. 1 in which front and rear waist regions 6, 7 have been disconnected from each other at the joining zones 4 and developed in directions indicated by the arrows P, Q extending in the back-and-forth direction and FIG. 5 is a sectional view taken along a line V-V in this plan view. As shown, the developed diaper 1 has its length as viewed in the vertical direction of FIG. 3 bisected by a transverse center line B-B extending in a direction which is orthogonal to the longitudinal center line A-A. In the developed state as shown in FIG. 4, the diaper 1 is substantially symmetric about the longitudinal center line A-A and may be folded back along the transverse center line B-B to obtain the diaper 1 in the state as shown in FIG. 1.

The covering component 2 comprises an hourglass-shaped inner sheet 16, a rectangular intermediate sheet 17 lying on the outer side of the inner sheet 16 and an outer sheet 18 lying on the outer side of the intermediate sheet 17. The inner sheet 16 is preferably made of breathable nonwoven fabric, more preferably made of hydrophobic breathable nonwoven fabric. The intermediate sheet 17 is preferably made of liquid-impervious plastic film, more preferably made of breathable but liquid-impervious plastic film and identical in shape as well as in size to the absorbing component 3. The outer sheet 18 is made of breathable nonwoven fabric and identical in shape as well as in size to the inner sheet 16. These sheets 16, 17, 18 are intermittently joined to one another by adhesion or heat-sealing to form the covering component 2. The nonwoven fabric layers forming the inner and outer sheets 16, 18 of the covering component 2 contribute to a soft touch of the diaper 1. The waist- and leg-circumferential elastic members 12, 13 interposed between the inner and outer sheets 16, 18 are attached to at least one of these sheets 16, 18 by means of an adhesive agent (not shown).

The absorbing component 3 comprises a core 21 and a cover sheet 22 and has a rectangular shape which is relatively long in the vertical direction as viewed in FIG. 4. This rectangular absorbing component 3 is contoured by transversely opposite lateral edges 26 extending parallel to the longitudinal center line A-A and front and rear ends 27 extending in the transverse direction of the diaper 1 orthogonal to the transversely opposite lateral edges 26. The core 21 has a rectangular shape as a whole and has an inner surface 23 facing the wearer's body, an outer surface 24 facing the wearer's clothes, opposite side surfaces 40a extending in the longitudinal direction and opposite end surfaces 40b extending across the front and rear waist covering regions 6, 7 in the transverse direction. The core 21 additionally has grooves 20r, 20s, 20t (See FIG. 5 also) extending along a chain line R (third folding guide) extending in coincidence with the transverse center line B-B, a chain line S (first folding guide) extending so as to describe V-shape from the central zone of the core 21 defined by the intersection of the longitudinal center line A-A and the transverse center line B-B toward the front waist covering region 6 to the opposite side surfaces 40a and a chain line T (second folding guide) extending so as to describe V-shape from the central zone of the core 21 defined by the intersection of the longitudinal center line A-A and the transverse center line B-B toward the rear waist covering region 7 to the opposite side surface 40a. These grooves 20r, 20s, 20t divide the core 21 into core elements 21a, 21b, 21c, 21d, 21e, 21f. The groove 20r and the groove 20s intersect with each other at an angle α while the groove 20r and the groove 20t intersect with each other at an angle β. While the angles α and β are illustrated to be equal of the invention to set these two angles to be different from each other. In the crotch covering region 8, the absorbing component 3 is narrower than this crotch covering region 8, so lateral marginal edges 8a of the crotch covering region 8 form leg-circumferential flaps 11a extending outward beyond the lateral edges 26 of the crotch covering region 8, which define the respective leg-holes 11.

The core 21 divided in the core elements 21a through 21f is formed by compressing water-absorbent material such as a fluff pulp and super-absorbent polymer particles under an appropriate pressure and, if desired, covering such a compressed material with a tissue paper or a nonwoven fabric of thermoplastic synthetic fibers modified to be hydrophilic. The inner surface 23 of the core 21 divided in the core elements 21a through 21f or the tissue paper or the like (not shown) covering this inner surface 23 may be joined to the cover sheet 22. The outer surface 24 of the core 21 or the tissue paper or the like covering this outer surface 24 may be joined to the inner sheet 16 by means of an adhesive agent 29a (See FIG. 5). The cover sheet 22 extends over the inner surface 23 in the transverse direction of the core 21 and reaches to the outer surface 24 in the vicinity of the respective side surfaces 40a beyond the side surfaces 40a. On the outer surface 24, lateral edge zones 22a of the cover sheet 22 are folded outward in the transverse direction of the core 21 and these lateral edge zones 22a folded in this manner are joined to the inner surface of the inner sheet 16 by means of a hot melt adhesive agent 29. Portions of the cover sheet 22 extending beyond the end surfaces 40b of the core 21 are bonded to the inner sheet 16 and layers of the sheet 22 overlaying each other are bonded together in the vicinity of these portions using a hot melt adhesive agent (not shown). Such cover sheet 22 is folded in a Z-shape or in an inverted Z-shape in the vicinity of the side surfaces 40a of the core 21 (See FIGS. 4 and 5). A stock material for the cover sheet 22 may be selected from the group consisting of a liquid-pervious nonwoven fabric, a perforated plastic film and a laminated sheet of the nonwoven fabric and the film.

The diaper 1 having the absorbing component 3 formed in this manner is folded back from the developed state shown in FIG. 4 along the transverse center line B-B and then the front and rear waist covering regions 6, 7 are connected to each other at the joining zones 4 to obtain the diaper 1 of FIG. 1. In this course, respective halves of the absorbing component 3 lying on both sides of the longitudinal center line A-A are folded toward this longitudinal center line A-A as shown in FIGS. 2 and 3. Specifically, the absorbing component 3 is folded along the groove 20r so that the outer surface 24 of the core element 21c is opposed to the outer surface 24 of the 21e (See FIG. 5) while the outer surface 24 of the core element 21d is opposed to the outer surface 24 of the core element 21f. At the same time, the absorbing component 3 is folded along the grooves 20s, 20t so that the inner surface 23 of the core element 21a is opposed to the inner surfaces 23 of the respective core elements 21c, 21d while the inner surface 23 of the core element 21b is opposed to the inner surfaces 23 of the respective core elements 21e, 21f (See FIG. 4). The grooves 20r, 20s, 20t serve an folding guides each extending from the transversely middle zone to each of the lateral edges 26 of the absorbing component 3 so as to describe generally V-shape in the portions of placed aside toward its front and rear ends, respectively. In the grooves 20r, 20s, 20t, there is little or no core 21. So the absorbing component 3 has its stiffness lower in these grooves 20r, 20s, 20t than in the other region. This unique arrangement facilitates the absorbing component 3 to be folded along the grooves 20r, 20s, 20t as shown in FIG. 2.

In the pull-on disposable diaper 1 of FIG. 1 arranged as has been described, the absorbing component 3 is folded at the opposite lateral edges 26, 26 so that the width of the absorbing component 3 may be reduced in the crotch covering region 8 and those opposite lateral edges 26, 26 extend upward. Accordingly, the diaper 1 comes in close contact with the wearer's crotch in the vicinity of the wearer's genital organs and an amount of urine is absorbent rapidly into the diaper 1 without spreading sideways. In addition, a space defined between these opposite lateral edges 26, 26 forms a pocket 30a depressed downward (See FIG. 3) serving to prevent a possibility that the inner surface 3a (See FIG. 5) of the absorbing component 3 wetted with absorbed urine might come in contact with the wearer's body over a large area and create an uncomfortable damp feeling against the wearer. Even if the body fluid flows beyond the lateral edges 26, the lateral marginal edges 8a of the crotch covering region 8 extending outward beyond the lateral edges 26 and defining the flaps 11a adapted to be tightened around the wearer's thighs function as barriers against leakage of the body fluids from the diaper 1. Furthermore, the outer surface 24 of the core 21 is covered with the liquid-pervious cover sheet 22 at least in the vicinity of the side surfaces 40a, so if any amount of body fluids flow beyond the peripheral edge of the absorbing component 3, such amount of body fluids will be introduced into outer pockets 30b (See FIG. 3) formed between the absorbing component 3 and the respective lateral marginal edges 8a of the crotch covering region 8 and absorbed by the core 21 through its outer surface 24. It should be noted here that the outer surface 24 of the core 21 may be at least partially, for example, in its transversely middle zone, covered with the liquid-impervious intermediate sheet 17 as shown in Figs.

In this diaper 1, as will be apparent from FIGS. 3, 4, 5, the lateral edge zones 22a of the cover sheet 22 are folded outward in the transverse direction of the absorbing component 3 and joined to the inner sheet 16 by means of the adhesive agent 29 and thereby movement of the core's region having been folded along the groove 20r to restore the state before folded, in other words, movement outward with respect to the diaper 1 is restrained. The movement outward with respect to the diaper is the movement in the direction indicated by the arrow Y in FIG. 3. It is believed that the movement of the region extending along the groove 20r in the direction of the arrow Y is restrained because the core elements 21c, 21e get nearer to each other and the core elements 21d, 21f get nearer to each other as the lateral edge zones 22a is deformed from its flat state as seen in FIG. 4 to its curved state as seen in FIG. 3. So far as such movement is restrained, the absorbing component 3 folded so as to become narrower in the crotch covering region 8 can be reliably kept in this folded configuration even after the diaper has been put on the wearer's body.

To put the diaper 1 on infant's body, his or her mother may guide the infant's legs through the waist-hole 9 opened as widely as possible with the mother's hands put against the inner side of the waist-hole 9 into the respective leg-holes 11. With this diaper 1, the absorbing component 3 provided separately of the covering component 2 in the crotch covering region 8 far from the waist-hole 9 is not affected by deformation of the diaper 1 occurring as the waist-hole 9 is opened in this manner. Furthermore, even if the lateral marginal edges 8a of the crotch covering region 8 moves due to broadening of the waist-hole 9, there is substantially no possibility that the absorbing component 3 gets out of its initial position since the lateral edges 26 of the absorbing component 3 are not joined to the lateral marginal edges 8a. In this way, there is not likely that the absorbing component 3 folded so as to be narrower in the crotch covering region 8 might get out of its desired shape and the lateral edges 26 of the absorbing component 3 extending upward are reliably brought in close contact with the infant's crotch. Therefore, the absorbing component 3 folded so as to reduce its width reliably provides its expected effect when the diaper 1 is put on the infant's body. Without departing from the scope of the invention, it is possible to eliminate provision of the groove 20r depending on a thickness of the core 21 and to fold the absorbing component 3 using the grooves 20s, 20t. It is also possible to locally press with or without heating the zones of the absorbing component 3 extending along the chain lines R, S, T or the chain lines S, T using embossing rolls or the like so that these zones may have stiffness higher than that in the other zone and the absorbing component 3 may be folded in parallel to these zones of relatively high stiffness.

The pull-on disposable diaper according to this invention has advantageous effects that the body fluid absorbing component folded inward in the transverse direction of the core in the crotch covering region to reduce the width of the core can be reliably maintained in such a folded state because the body fluid absorbing component comprising the body fluid absorbing core and the liquid-pervious cover sheet have the transversely opposite lateral marginal edges folded back on the outer surface of the core outward in the transverse direction of the core.

What is claimed is:
1. A disposable diaper, comprising:
a cover comprising opposite inner and outer surfaces, said cover further comprising longitudinally opposite front and rear waist regions and a crotch region extending between said front and rear waist regions; and a body fluid absorbing component extending from said crotch region into said front and rear waist regions, said body fluid absorbing component comprising a liquid absorbent core and a liquid-pervious cover sheet;
wherein said body fluid absorbing component, in said crotch region, has transversely opposite portions being tucked inwardly of said diaper;

said cover sheet comprises a first section covering an inner surface of said core, a second section covering an opposite, outer surface of said core, and a third section disposed between said second section and the inner surface of said cover, said third section being joined to the inner surface of said cover, said cover sheet further comprising a first folded section connecting said first and second sections and a second folded section connecting said third and second sections;

said second folded section is present not only in the inwardly tucked portions of the body fluid absorbing component, but also outside said inwardly tucked portions;

said body fluid absorbing component, in said crotch region, is folded along a pair of first fold guiding lines extending from a transversely middle zone of said crotch region toward said front waist region and describing a V shape;

said body fluid absorbing component, in said crotch region, is further folded along a pair of second fold guiding lines extending from said transversely middle zone of said crotch region toward said rear waist region and also describing a V shape; and each of the inwardly tucked portions of said body fluid absorbing component is defined between one of said first fold guiding lines and one of said second fold guiding lines.

2. The disposable diaper according to claim 1, wherein said cover is free of and not folded along said first and second fold guiding lines.

3. The disposable diaper according to claim 1, wherein at least one of said fold guiding lines is formed as a groove in said core, and a stiffness of said core is lower within said groove than outside said groove.

4. The disposable diaper according to claim 1, wherein said core comprises a zone having a stiffness higher than in a remainder of said core, and at least one of said first and second fold guiding lines is formed in parallel with said zone.

5. The disposable diaper according to claim 1, wherein a first angle at an apex of the V shape of said first fold guiding lines is different from a second angle at an apex of the V shape of said second fold guiding lines.

* * * * *